US006845651B2

(12) United States Patent
Gupta et al.

(10) Patent No.: US 6,845,651 B2
(45) Date of Patent: Jan. 25, 2005

(54) QUICK BET METHOD AND APPARATUS FOR DETERMINING SURFACE AREA AND PORE DISTRIBUTION OF A SAMPLE

(75) Inventors: Krishna M. Gupta, Ithaca, NY (US); Akshaya Jena, Ithaca, NY (US); Ronald V. Webber, Dryden, NY (US); Chandrashekar Venkataraman, Richmond, VA (US)

(73) Assignee: Porous Materials, Inc., Ithaca, NY (US)

( * ) Notice: Subject to any disclaimer, the term of this patent is extended or adjusted under 35 U.S.C. 154(b) by 0 days.

(21) Appl. No.: 10/419,501

(22) Filed: Apr. 21, 2003

(65) Prior Publication Data

US 2004/0206161 A1 Oct. 21, 2004

(51) Int. Cl.$^7$ .............................................. G01N 15/08
(52) U.S. Cl. ......................................................... 73/38
(58) Field of Search .............................................. 73/38

(56) References Cited

U.S. PATENT DOCUMENTS

| | | | |
|---|---|---|---|
| 2,465,948 A | | 3/1949 | Welge |
| 2,534,737 A | | 12/1950 | Rose |
| 2,612,036 A | | 9/1952 | Angona |
| 2,706,904 A | | 4/1955 | Hertel |
| 2,755,660 A | | 7/1956 | Kammermeyer et al. |
| 2,788,657 A | * | 4/1957 | Innes .............................. 73/38 |
| 3,262,319 A | * | 7/1966 | Orr, Jr. et al. ................... 73/38 |
| 4,112,738 A | * | 9/1978 | Turner ........................ 73/32 R |
| 4,149,402 A | * | 4/1979 | Manes ........................ 73/19.12 |
| 4,203,317 A | | 5/1980 | Gupta |
| 4,217,336 A | | 8/1980 | Maire et al. |
| 4,489,593 A | * | 12/1984 | Pieters et al. ................... 73/38 |
| 4,576,927 A | | 3/1986 | Kuroda et al. |
| 4,660,412 A | | 4/1987 | Gupta |
| 4,718,270 A | * | 1/1988 | Storr .............................. 73/38 |
| 4,744,240 A | | 5/1988 | Reichelt |
| 5,263,360 A | * | 11/1993 | Blauch et al. ................... 73/38 |
| 5,373,727 A | * | 12/1994 | Heller et al. .................... 73/38 |
| 5,442,950 A | * | 8/1995 | Unalmiser et al. ............. 73/38 |
| 5,695,818 A | | 12/1997 | Soffer et al. |
| 5,696,198 A | | 12/1997 | Chereisky et al. |
| 5,955,185 A | | 9/1999 | Yoshino et al. |

FOREIGN PATENT DOCUMENTS

| | | | |
|---|---|---|---|
| DE | 1927171 | 12/1970 | .......... G01N/13/04 |
| DE | 19858338 | 12/1997 | .......... G01N/15/08 |
| EP | 0139202 | 5/1985 | .......... G01N/15/08 |
| EP | 0831318 | 3/1998 | .......... G01N/15/08 |
| RU | 229002 | 2/1969 | .................... 73/38 |
| RU | 853492 | 8/1981 | .................... 73/38 |
| RU | 1130772 | 12/1984 | .................... 73/38 |
| RU | 1807341 | 4/1993 | .................... 73/38 |

OTHER PUBLICATIONS

Jena, Akshaya K. and Gupta, Krishna M., "In–Plane Compression of Battery Separators," Journal of Power Sources 80, 1999, p. 46–52, no month.

(List continued on next page.)

Primary Examiner—Michael Cygan
(74) Attorney, Agent, or Firm—Brown & Michaels, PC

(57) ABSTRACT

A pressurizable sample chamber of known volume holds a sample with unknown porosity characteristics. The sample chamber has a known pressure (or vacuum). A flow controller preferably controls the flow of the pure gas to be adsorbed by the sample in the sample chamber. A pressure monitor preferably monitors the pressure in the sample chamber. Once the pressure approaches a target pressure, the flow controller is closed. The pressure monitor continues to monitor the pressure until it stops changing when an equilibrium is attained. The amount of gas introduced into the system through the flow controller and the volume and final pressure of the sample chamber are used to calculate the amount of gas adsorbed. This calculation is subsequently used to determine the porosity characteristics of the sample. Some of these characteristics include, but are not limited to, pore distribution and surface area.

11 Claims, 3 Drawing Sheets

OTHER PUBLICATIONS

Gupta, Vibhor and Jena, A.K., "Substitution of Alcohol in Porometers For Bubble Point Determination."

Advances in Filtration and Separation Technology, col. 13b, 1999, p. 833–844, no month.

Gupta, Nalini and Jena, Akshaya. "Measuring in Layers: Determining the Pore Structure of Individual Layers of Multi–Layered Ceramic Composites." Ceramic Industry, Feb. 2001, p. 28–33.

Jena, Akshaya K. and Gupta, Krishna M. "Determination of Pore Volume and Pore Distribution by Liquid Extrusion Porosimetry Without Using Mercury" Ceramic Engineering and Science Proceedings, 2002, p. 277–284.

Thelen, E. "Soil Permeability Tester", Franklin Institute Laboratories Notes: Franklin Inst. Journal, vol. 253, Apr. 1952, pp. 340–341.

"DWI—LB74 Porosity" http://www.dwi.twth–aachen.de/ib/74.html. Dec. 27, 1997.

Jena Akshaya K. and Gupta, Krishna M. "A Novel Mercury Free Technique for Determination of Pore Volume, Pore Size and Liquid Permeability." P/M Science & Technology Briefs, vol. 4, No. 1, 2002, pp. 5–8.

Jena, Akshaya K. and Gupta, Krishna M. "Materials Pore-Sight Testing Pore Volume and Flow Through Porous Materials" Materials World, The Journal of the Institute of Materials, vol. 10, Num. 2, Feb. 2002.

* cited by examiner

QUICK BET METHOD AND APPARATUS FOR DETERMINING SURFACE AREA AND PORE DISTRIBUTION OF A SAMPLE

BACKGROUND OF THE INVENTION

1. Field of the Invention

The invention pertains to the field of porosimetry, or the measurement of the surface area and porosity of substances. More particularly, the invention pertains to a quick-BET method and apparatus for determining the surface area and porosity characteristics of a sample.

2. Description of Related Art

There are two prior art methods for measuring the adsorption of a gas in a sample to determine the surface area and pore distribution of that sample. The first method is a BET (Brunauer, Emmett, Teller) static volumetric technique. In this method, gas (5) is first introduced into chamber (1). The gas (5) contained in chamber (1) is allowed to flow through an open valve (4) from a first sealed chamber (1) containing gas at a known pressure to a second sealed chamber (2). Both chambers (1) and (2) have a known volume. Chamber (2), which is at a constant temperature and a certain known pressure, contains a sample (3) with a plurality of pores (6).

Once a certain volume of the gas has been introduced, the pressures in the chambers are allowed to come to equilibrium. The pressure changes in the two chambers are measured. The pressure changes in the two chambers and their volumes provide the amount of gas adsorbed.

Once the amount of gas adsorbed at each pressure is calculated, this measurement can be used to determine the pore distribution and surface area of the sample using calculation methods known in the art.

This method is very accurate because it permits complete static equilibrium rather than a steady state and there is no possible interference in the adsorption of the gas because the pure gas rather than a mixture of gases is used. However, this method usually requires several steps in the experimental procedure. Therefore, a lot of instrumentation may be required and the test may be time consuming.

An alternative method is the differential flow technique, which is faster, but less accurate than the volumetric technique. In this method, a mixture (23) of two gases (21) and (22) with a known composition is pumped into a chamber (20), which contains the sample (3). The sample (3) selectively adsorbs one of the gases. A mixture (24) of the first gas (21) and the second gas (22) with a second composition exits the chamber.

Flow continues until there is no longer a change in the composition of the mixture (24) coming out of the system. The compositions of gases and flow rates are continuously measured. These measurements are used to determine how much gas was adsorbed. The calculated gas adsorbed is then used to determine surface area and pore distribution of the sample, by methods known in the art.

SUMMARY OF THE INVENTION

The apparatus of the present invention includes a pressurizable sample chamber of known volume, which holds a sample with unknown porosity characteristics. The sample chamber has a known pressure (or vacuum). A flow controller preferably controls the flow of the pure gas to be adsorbed by the sample in the sample chamber. The sample chamber does not permit the gas to flow out. A pressure monitor preferably monitors the pressure in the sample chamber. Once the pressure approaches a target pressure, the flow controller is closed. The pressure monitor continues to monitor the pressure until it stops changing when equilibrium is attained. The amount of gas introduced into the system through the flow controller and the volume and final pressure of the sample chamber are used to calculate the amount of gas adsorbed. This calculation is subsequently used to determine the porosity characteristics of the sample. Some of these characteristics include, but are not limited to, pore distribution and surface area.

A method of the present invention begins with the sample chamber at a known pressure (or vacuum). Pure gas is introduced into the sample chamber until the pressure approaches a target pressure. Then, an amount of gas introduced into the system is determined, and the pressure is monitored until it reaches an equilibrium.

DETAILED DESCRIPTION OF THE INVENTION

The apparatus of the present invention overcomes the shortcomings of the prior art to create a fast reading, which is accurate, requires minimal instrumentation, is less expensive, and compact.

In the prior art volumetric method, gas is introduced to the sample chamber from gas storage chamber (1) in steps. After each step the gas in the sample chamber is adsorbed. Therefore, multiple steps are required to attain the required final pressure in the sample chamber. After each step, it may also become necessary to introduce more gas to the storage chamber (1) and measure pressure before the following test. The amount of gas introduced into the sample chamber is computed from pressures and volumes of gas in the two chambers measured after each step.

In contrast, these difficulties are avoided in the present invention. The gas is adsorbed as it is introduced. Consequently, the final pressure in the sample chamber is quickly attained. There are no multiple steps. The amount of gas introduced into the sample chamber is obtained by integration of the flow rate over time. Therefore, the apparatus and method of the present invention are faster and require less instrumentation.

The prior art, differential flow method uses a mixture of gases and requires frequent gas analysis. The present invention uses a pure gas and does not require any gas analysis. Consequently, the results are more accurate. Also, the present invention is faster and requires less instrumentation.

Figure 1:
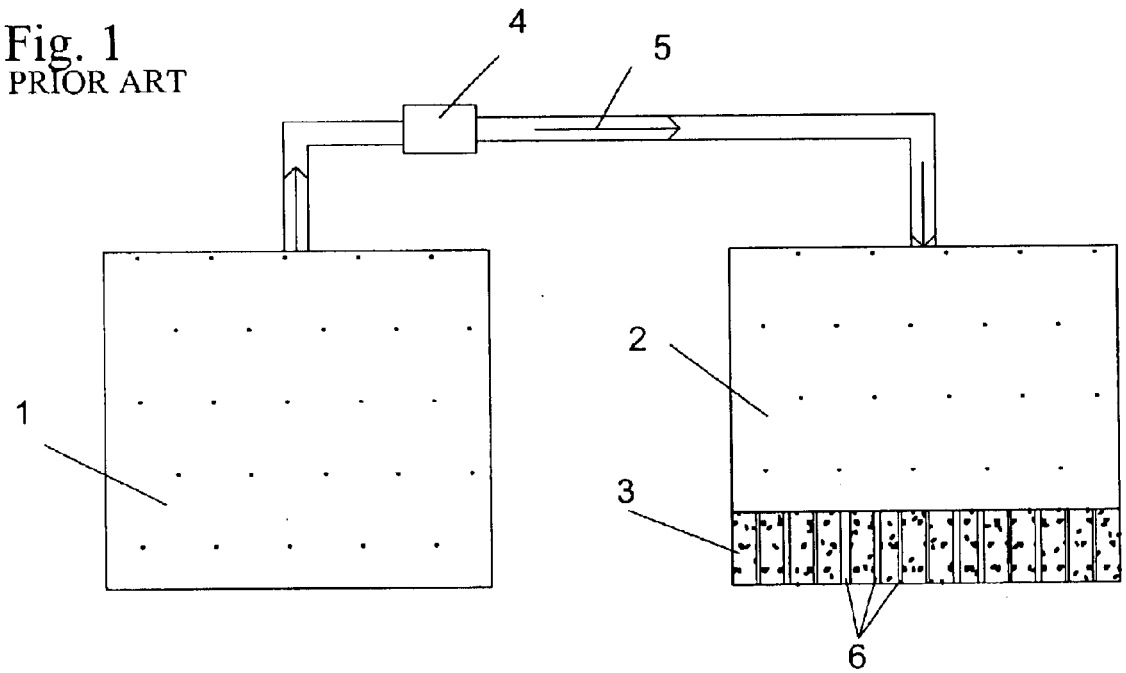
FIG. 1 shows an apparatus for using the volumetric technique as known in the prior art.
Figure 2:
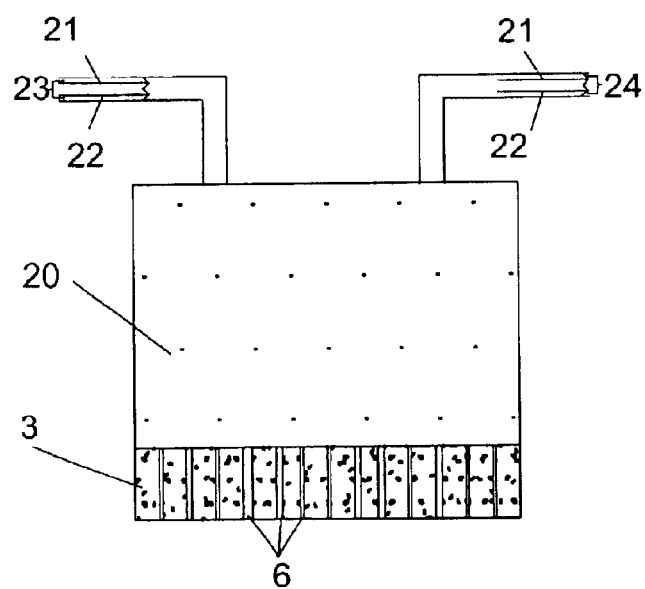
FIG. 2 shows an apparatus for using the flow technique as known in the prior art.
Figure 3:
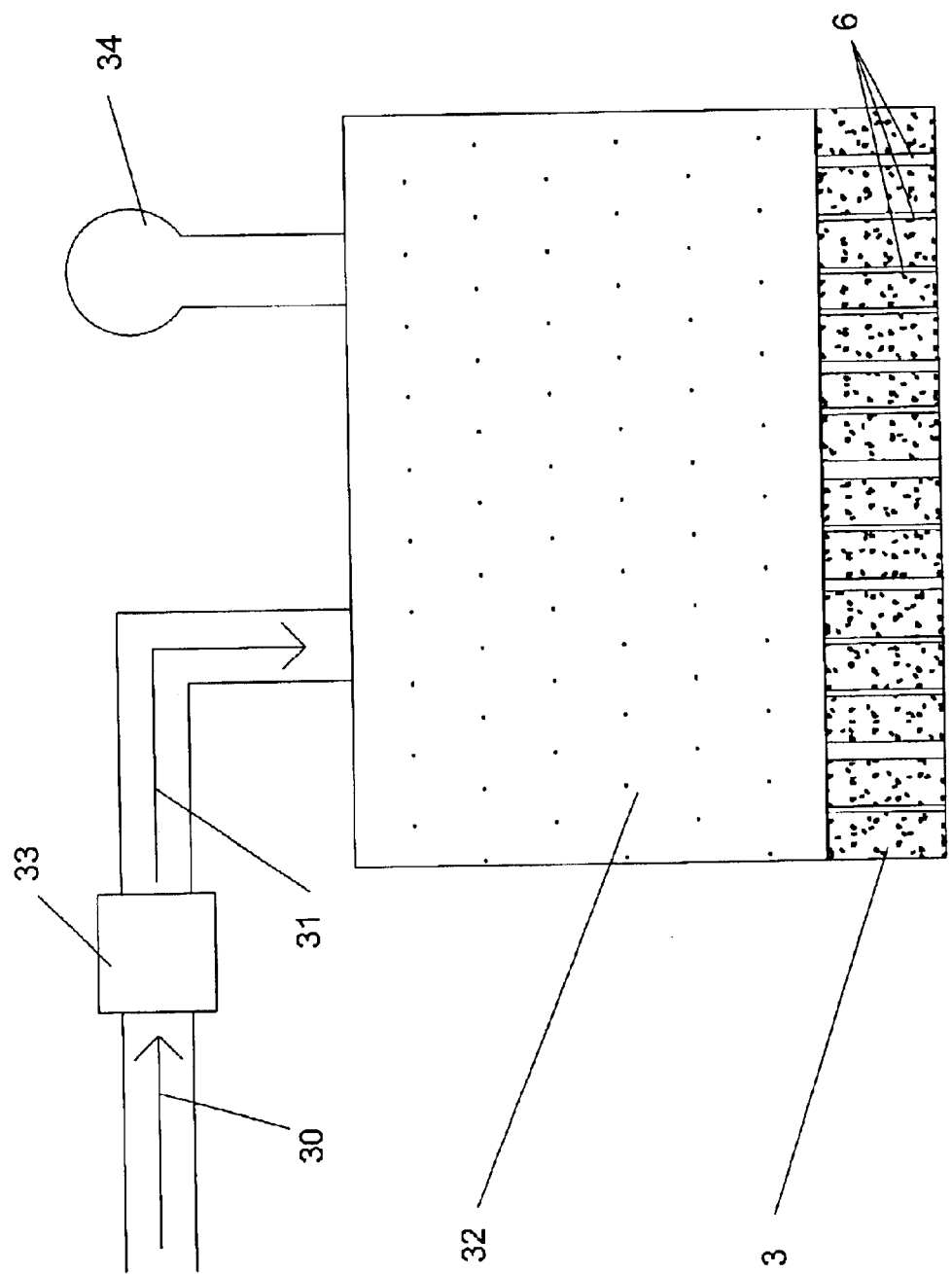
FIG. 3 shows an apparatus for using the quick-BET method of the present invention.

FIG. 3 shows an embodiment of the apparatus of the present invention. Pure gas (30) is pumped (31) into a sealed chamber (32) containing a sample (3). While the invention is described in the context of pure gases, the scope of the invention is intended to include pure gases and vapors, which are gaseous phases of substances existing as solids and liquids. Some examples of the gas include, but are not limited to, nitrogen, krypton, hydrogen, carbon monoxide and carbon dioxide. The chamber (32) has a known pressure (or vacuum).

A flow meter, or preferably flow controller (33), controls the gas flow so that it flows at a known rate, for example at a certain number of moles/minute. In a preferred embodiment, the flow rate is controlled with a commercial flow controller. In a preferred embodiment, a Teledyne® flow controller HFC-202 is used.

A pressure monitor (34) monitors the pressure. In a preferred embodiment, the pressure monitor (34) is MKS Barotron Model-722A-22564. Once the pressure approaches a target pressure, the flow controller (33) is closed. The pressure monitor (34) continues to monitor the pressure until the target pressure is reached, and the pressure stops changing because it has reached an equilibrium. This is done using a feed back loop. Use of the loop reduces the testing time considerably.

Integration of the flow controller and pressure changes are used to calculate the amount of gas adsorbed. This calculation is subsequently used to determine the porosity characteristics of the sample. Some of these characteristics include, but are not limited to, surface area, pore volume, pore distribution, and adsorption isotherms.

Figure 4:
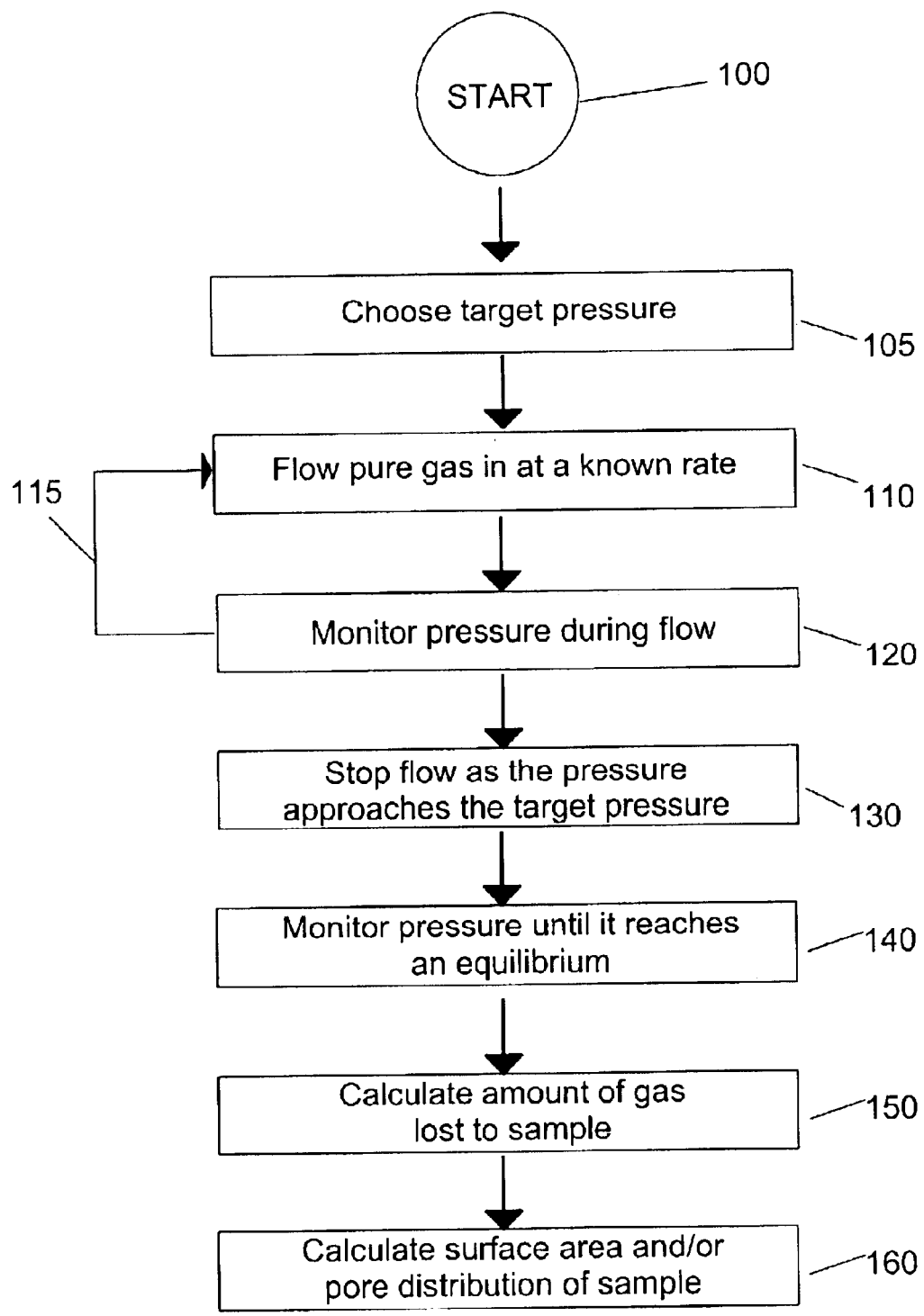
FIG. 4 shows a flowchart of the method of the present invention.

FIG. 4 shows a flowchart of a preferred embodiment of the method of the present invention.

The method begins with the sealed chamber (32) at a known pressure (or vacuum) in step (100). A target pressure is chosen in step (105).

Pure gas (30) is pumped (31) into the chamber (32) at a known rate in step (110). A flow controller (33) is preferably used during this step to control and measure the flow rate of the gas.

The pressure in the chamber (32) is monitored by the pressure monitor (34) in step (120). This step preferably takes place simultaneously with step (110).

A feed back loop is preferably used to reduce the flow rate such that when the pressure approaches the target pressure chosen in step (105), the flow controller (33) is closed, and the flow of gas into the chamber (32) ceases in step (130). Since the flow controller (33) controlled the amount of gas flow into the chamber (32), the total amount of gas introduced into the system is known.

The pressure continues to be monitored in step (140), until the pressure reaches an equilibrium. The pressure of the gas in the system, which has a known volume, is measured after adsorption.

The amount of gas adsorbed by the sample is calculated in step (150) using the pressure at equilibrium, volume of the chamber, temperature of the chamber and the amount of gas introduced into the chamber through the flow controller.

Amount of gas introduced to the sample chamber containing the sample under vacuum, $N_1$ moles=Obtained by integration of the flow controller Amount of gas left in the sample chamber after equilibration, $N_2$ moles=Obtained from pressure, volume and temperature of sample chamber.

Therefore, $N_1-N_2$ was adsorbed by the sample.

The calculation in step (150) is then used to determine porosity characteristics, which include surface area and pore distribution, in the sample in step (160) by methods known in the art.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of evaluating the porosity characteristics of a sample of material having a plurality of pores using an apparatus comprising a pressurizable sample chamber of a known volume for holding the sample, wherein the sample chamber is at a known pressure and the sample chamber does not permit the gas to flow out, comprising the steps of:

a) introducing pure gas into the sample chamber and increasing the pressure to quickly approach a final target pressure by utilizing a feedback system, which reduces a flow rate over time such that when the pressure approaches the target pressure, a flow of gas into the chamber ceases;

b) determining an amount of gas introduced into the system by integrating the flow rate over time; and c) monitoring the pressure over time, after gas flow ceases and until the system reaches an equilibrium.

2. The method of claim 1, further comprising, after step c), the step of:

d) calculating an amount of gas adsorbed by the sample using a pressure change determined at equilibrium.

3. The method of claim 2, further comprising, after step d), the step of:

e) calculating at least one porosity characteristic of the sample using the calculation of gas adsorbed from step d).

4. The method of claim 1, wherein the gas is selected from the group consisting of nitrogen, krypton, hydrogen, carbon monoxide, and carbon dioxide.

5. The method of claim 1, wherein the porosity characteristic being evaluated is selected from the group consisting of surface area, pore volume, pore distribution, and adsorption isotherms.

6. The method of claim 1, wherein a flow controller introduces the gas into the sample chamber at a known rate.

7. An apparatus for evaluating the porosity characteristics of a sample of material having a plurality of pores comprising:

a) a pressurizable sample chamber for holding the sample;

b) a conduit connected to the chamber, wherein the conduit delivers gas into the chamber;

c) a flow controller coupled to the conduit, wherein the flow controller controls and measures an amount of gas entering the chamber through the conduit; and d) a feedback system controlling the flow controller, which reduces a flow rate such that when a pressure in the sample chamber approaches a final target pressure, a flow of gas into the chamber ceases.

8. The apparatus of claim 7, further comprising:

e) a pressure monitor for monitoring the pressure in the chamber.

9. The apparatus of claim 8, wherein the pressure monitor is coupled to the chamber.

10. The apparatus of claim 7, wherein the gas is selected from the group consisting of nitrogen, krypton, hydrogen, carbon monoxide, and carbon dioxide.

11. The apparatus of claim 7, wherein the porosity characteristic being evaluated is selected from the group consisting of surface area, pore volume, and pore distribution.

* * * * *